United States Patent [19]

Forchetti

[11] Patent Number: 4,517,997

[45] Date of Patent: May 21, 1985

[54] HAIR IMPLANT STRUCTURE

[76] Inventor: A. Patrick Forchetti, 1412 Wharton St., Philadelphia, Pa. 19146

[21] Appl. No.: 100,899

[22] Filed: Dec. 6, 1979

[51] Int. Cl.³ .............................................. A41G 3/00
[52] U.S. Cl. ................................................ 132/5; 3/1
[58] Field of Search .................................... 132/5; 3/1

[56] References Cited

U.S. PATENT DOCUMENTS 3,119,398  1/1964  Bennett et al. ......................... 132/5
3,811,425  5/1974  Widdifield ............................... 3/1

Primary Examiner—Gregory E. McNeill
Attorney, Agent, or Firm—Weiser & Stapler

[57] ABSTRACT

A hair implant structure includes artificial or natural hairs which are each downwardly enlarged to approximate the configuration of a natural hair root. The lower end of the hair structure including the enlarged portion is coated with an inert material, such as gold, to minimize chances of infection after implant.

8 Claims, 3 Drawing Figures

HAIR IMPLANT STRUCTURE

BACKGROUND OF THE INVENTION

This invention relates generally to the field of hair implant structures, and more particularly, is directed to a hair filament which may be artificial or natural and which is suitable for implanting in the human scalp.

Baldness in human beings has always created personal problems in view of the cosmetically undesirable appearance sometimes presented by individuals who have lost some or most of their hair. Prior workers in the art have attempted to treat this problem in many ways, for example, by providing toupees, by employing hair weaving techniques, by the transplantation of living hair including surgically removing and reapplying plugs of hair and other methods. Hair weaving has often proved disadvantageous in that such weavings have generally required frequent tightenings to remain pleasing in appearance. While hair transplants have the advantages inherent with a person having his own hair installed, experience has shown that such transplanted hair does not spread over the scalp and each given area continues to require individual treatment.

Other structures and methods have been developed by workers in this field which include the implantation of nonliving natural hairs or synthetic hairs into the scalp. Such an approach is surgical in nature and has created problems directly relating to possible rejection of the hair structure or perhaps by increasing the chance of infection caused by the interaction by the implanted structure and the natural scalp. In view of the difficulties experienced by the prior workers, the need remains for a reliable, surgically pure and aesthetically pleasing hair implanting method and structure.

SUMMARY OF THE INVENTION

It is therefore an object of the present invention to provide an improved hair implant structure of the type set forth.

It is another object of the present invention to provide a novel hair implant structure suitable for firm implantation directly under the epidermis of the human scalp without causing rejection in the surrounding tissue.

It is another object of the present invention to provide a novel hair implant structure comprising either natural hair or artificial hair suitable to be implanted directly under the epidermis without creating medical complications for the recipient.

With these and other objects in view, the invention provides a novel hair implant structure suitable for implant in living skin which comprises filament equipped with a structure that is similar in configuration to a natural hair root for anchoring the hair structure below the surface of the skin. The hair structure also includes an uninterrupted base coating or covering of inert material such as gold to discourage rejection and to substantially prevent infection at the site of implantation.

The hair employed may be natural human hair or animal hairs of suitable color and texture or may be artificial hair fabricated of suitable materials, for example, plastic resins, such as nylon. The root is formed to the desired configuration of the same resin as the filament and may be connected to a natural or artificial filament by a suitable, known bonding agent or by other known methods.

The hair to be implanted, either natural or synthetic, can be matched in color, diameter and texture to the hair of the recipient and will be coated at the base with gold or other inert, noninfectious material. Preferably, the root and lower section of the filament is completely covered for a distance sufficient to extend to the surface of the scalp after implantation. By carefully placing the gold coated hairs into the scalp in known manner, one at a time, an even, perfectly natural appearing head of artificial or natural head can be implanted upon the bald areas of the scalp. Of course, as more and more hairs are so implanted, a fuller and more natural appearance can be created.

A more complete understanding of the invention will be had by referring to the following description and claims of a preferred embodiment thereof, taken in conjunction with the accompanying drawings, wherein like reference characters refer to similar parts throughout the several views and in which:

DESCRIPTION OF THE PREFERRED EMBODIMENT OF THE INVENTION

Figure 1:
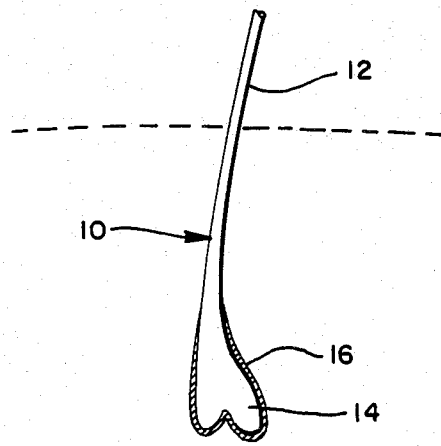
FIG. 1 is an elevational view showing a hair implant structure including an inert coating covering an enlarged portion of the base.

Although specific terms are used in the following description for the sake of clarity, these terms are intended to refer only to the particular structure of the invention selected for illustration in the drawings, and are not intended to define or limit the scope of the invention.

Figure 2:
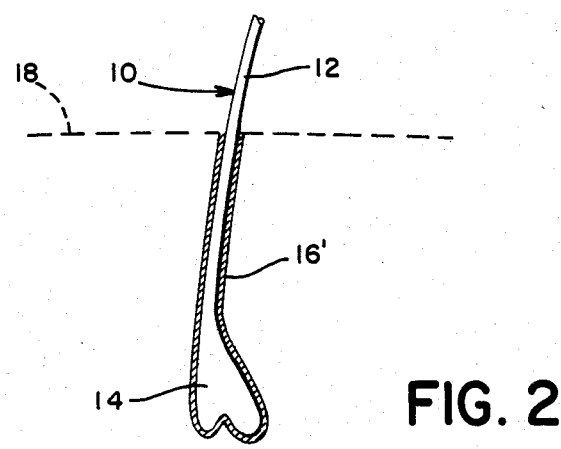
FIG. 2 is an elevational view similar to FIG. 1 showing a hair implant structure including an inert base coating covering an enlarged portion of the base and extending upwardly to the surface of the skin.
Figure 3:
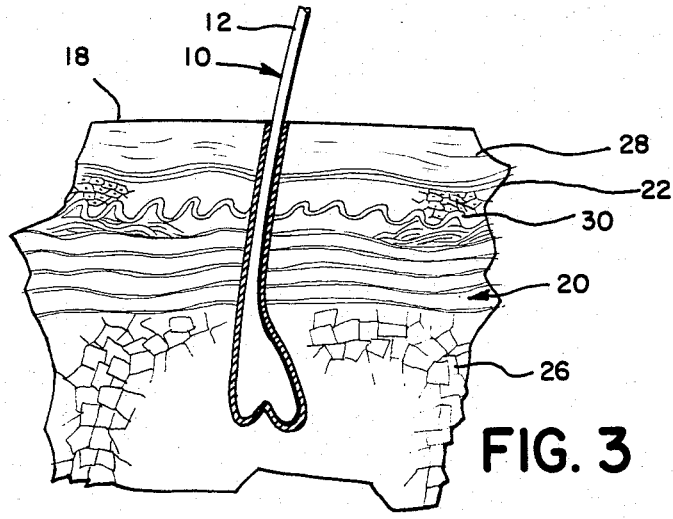
FIG. 3 is a vertical, sectional view of an individual hair implant structure in accordance with the invention, shown in place in a human scalp.

Referring now to the drawings, there is shown in FIGS. 1 and 2 a hair implant structure generally designated 10 which includes an elongated filament 12 which may be natural human or animal hair or which may be fabricated of a suitable plastic material to the desired configuration, texture and color.

The filament 12 terminates downwardly in an enlarged root 14 which is securely affixed to the filament in a manner to simulate a natural hair root. The enlargement provided by the root 14 serves to secure the hair implant structure to the skin tissue 20 after implantation to thereby discourage disassociation of the hair structure from the scalp either by naturally falling out or by being pulled out.

It is an essential part of this invention to coat or cover the lower or base portion of the hair implant structure with an inert material so as to prevent infection or rejection of the structure after implantation in skin 20. In accordance with the teachings of this invention, the enlarged root 14 is completely covered with a thin coating of inert material 16, for example, gold. See FIG. 1. In a preferred embodiment, as illustrated in FIG. 2, the entire lower portion of the filament is protected by a thin coating of gold 16' complete and uninterrupted from the bottom of the root through the entire implant length, that is all of the lower part of the filament that will be implanted below the skin surface 18.

Inasmuch as the color of gold may be varied within known limits by using known techniques, if necessary for any reason to extend the gold coating 16' above the surface 18 of the skin, the color of the hair can be substantially duplicated in the gold coating, to thereby provide a more aesthetically pleasing appearance.

In order to use the hair implant structure 10 of the present invention, a sufficient number of filaments 12 are provided with securely affixed roots 14 and then the lower portions are completely coated with inert material, such as gold 16,16'. If desired, the gold coating can be treated to correspond to the color of the filament. A known skin piercing device (not shown) in the nature of a sterile needle is then utilized to puncture the surface 18 of the skin 20 and to form a hair implant structure receiving opening through the epidermis 22 comprising the stratum corneum 28 and stratum germanatinum 30 and into the subcutaneous tissue 26.

A hair implant structure 10 is then inserted downwardly into the opening thus formed root first so that the gold coating 16,16' is in intimate overall contact with the living tissue of the skin 20. A sufficient number of hair implant structures 10 should be utilized to present an appearance that is similar to natural hair. Accordingly for the individual that is receiving the hair implant, the distance from one implanted structure to the next is most important in achieving a natural appearance. Structure 10 after structure 10 is individually implanted in the skin 20 until the desired effect is achieved. After implantation, the natural healing effects of the skin 20 will act to close the openings about the filaments 12 and the inert coatings 16,16' to thereby secure the structures in place. By placing the coated hairs into the scalp one at a time, an even, perfectly naturally appearing head of artificial or natural hair can be placed and secured on a scalp.

Although the invention has been described with a certain degree of particularity, it is understood that the present disclosure has been made only by way of example and that numerous changes in the details of construction and the combination and arrangement of parts may be resorted to without departing from the scope of the invention.

What is claimed is:

1. In a hair implant structure for implanting below the skin surface, the combination of
    an elongate, thin, filament of natural or artificial hair, said filiment having a bottom end for implanting into the skin;
    an enlargement secured to the filiment at the bottom end thereof; and
    an inert coating applied to the bottom end and covering at least the enlargement, said inert coating being the outermost layer in the so-coated portion of the structure.

2. The hair implant structure of claim 1 wherein the inert coating covers the bottom end for a distance that is sufficient to extend at least from the bottom of the enlargement to the surface of the skin after the structure is implanted in the skin.

3. The hair implant structure of claims 1 or 2 wherein the inert coating is gold.

4. The hair implant structure of claim 1 wherein the enlargement is fabricated of the same material as the filiment.

5. In a non-infectious method of implanting hair structure in a human scalp to achieve a natural appearance by simulating the appearance of other hairs in place in the scalp, the steps of
    forming enlargements and securing one enlargement respectively to the bottom end of each of a plurality of natural or artificial hair filiments;
    coating the bottom ends including the enlargements with an inert non-infectious material;
    piercing openings one at a time in the skin downwardly from the skin surface for distances each sufficient to receive the enlargement;
    spacing the respective openings apart distances substantially equal to the distances between the hairs already in place in the scalp; and
    implanting hair structures individually into a respective opening with the applied coatings forming the outermost layer on the structures and thereby being interposed between the skin and each filiment.

6. The method of claim 5 wherein the non-infectious material is gold.

7. The method of claim 5 wherein the enlargement is fabricated of the same material as the filiment.

8. The method of claim 5 and the further step of healing the scalp at the said openings to close the openings about the enlargements to lock the hair structure to the skin.

* * * * *